United States Patent [19]
Brinks et al.

[11] Patent Number: 5,237,054
[45] Date of Patent: Aug. 17, 1993

[54] STABILIZED AQUEOUS COMPOSITION CONTAINING ANTIBODIES

[75] Inventors: Gerrit J. Brinks; Maria M. F. Mentink, both of Oss, Netherlands

[73] Assignee: Akzo Pharma, Arnhem, Netherlands

[21] Appl. No.: 772,636

[22] Filed: Oct. 8, 1991

Related U.S. Application Data

[63] Continuation of Ser. No. 157,421, Feb. 17, 1988, abandoned.

[30] Foreign Application Priority Data

Feb. 20, 1987 [NL] Netherlands ............... 8700422

[51] Int. Cl.$^5$ .................. A61K 35/14; C07K 5/00
[52] U.S. Cl. ............... 530/388.1; 530/306; 530/313; 530/388.24; 530/395; 530/397; 530/398; 530/399; 424/85.8
[58] Field of Search ............ 530/388.1, 388.8, 124, 530/395, 398, 399, 397, 306, 313; 424/85.8

[56] References Cited

U.S. PATENT DOCUMENTS

| | | | |
|---|---|---|---|
| 4,186,192 | 1/1980 | Lundblad et al. | 424/85.8 |
| 4,806,524 | 2/1989 | Kawaguchi et al. | 530/395 |

FOREIGN PATENT DOCUMENTS

| | | |
|---|---|---|
| 0132488 | 2/1985 | European Pat. Off. |
| 0170983 | 2/1986 | European Pat. Off. |
| 0173648 | 3/1986 | European Pat. Off. |
| 8400890 | 3/1984 | World Int. Prop. O. |

OTHER PUBLICATIONS

Arakawa et al, *Biochemistry,* vol. 21, pp. 6536–6544, 1982.

*Primary Examiner*—Michael G. Wityshyn
*Assistant Examiner*—Abdel A. Mohamed
*Attorney, Agent, or Firm*—William M. Blackstone

[57] ABSTRACT

A stabilized aqueous antibody composition comprising dextran as a stabilizer in an amount sufficient to prevent deactivation of the monoclonal antibodies at a temperature in the range of 4° to 40° C.

21 Claims, No Drawings

STABILIZED AQUEOUS COMPOSITION CONTAINING ANTIBODIES

This is a continuation of application Ser. No. 07/157,421 filed Feb. 17, 1988, now abandoned.

FIELD

The present invention relates to a stable aqueous composition containing one or more antibodies.

STATEMENT OF THE ART

Antibodies are nowadays frequently used in human and veterinary medicine for prophylactic, diagnostic or therapeutic purposes. Antiviral or antibacterial antibodies are being used in the (prophylactic) treatment of infectious diseases, antigonadotrophins are frequently used to regulate hormone levels and antibodies against tumor-antigens to localize and to combat tumors.

There is therefore a great need for stable aqueous preparations which contain antibodies and which can be injected directly into human beings or animals without further operations or treatments.

The basic problem is, however, that aqueous compositions of antibodies are in practice found to be particularly unstable and no longer have any, or virtually do not have any, antibody activity even after a very short period of time.

An obvious approach to solving this problem might be to freeze-dry the composition concerned.

However, even freeze-drying of the composition has been found not to yield the desired result. Irreversible dimerization of the antibodies concerned during the freeze-drying process is found to be a frequently occurring secondary reaction so that even the freeze-dried compositions suffer a considerable loss in activity. In addition, dimers or higher oligomers cause anaphylactic reactions in human beings which are, of course, undesirable.

There has therefore been a search for substances which, when added to the aqueous composition of the antibodies, ensure that the biological activity and the physical quality of the antibodies remain virtually constant over a long period.

During this investigation a large number of substances was investigated but none of the substances was found to bring about the desired stability of the antibodies in question to a sufficient extent.

SUMMARY OF THE INVENTION

It has now been found that an aqueous composition of one or more antibodies remains stable over a long period of time if dextran is added to the aqueous composition.

DESCRIPTION OF THE PREFERRED EMBODIMENT

The term dextran comprises a group of water-soluble polysaccharides having a mean molecular weight varying from approximately 20,000 to approximately 150,000 such as described, for example, in the Merck Index, 10th edition, No. 2911. Very suitable representatives within the scope of the present invention are dextrans with the relatively low molecular weight of approximately 20,000 to 75,000 such as dextran 40 having a mean molecular weight of 40,000 and dextran 70 (molecular weight 70,000).

The antibodies which are stabilized according to the present invention can, for example, be obtained from antiserum (polyclonal antibodies), or may be produced by immortalized B-lymphocytes e.g. according to the method described by Köhler and Milstein, Nature 256, 495(1975) resulting in monoclonal antibodies, or may be obtained from trioma's or quadroma's yielding bivalent monoclonal antibodies. Monoclonal antibodies obtained through recombinant DNA techniques are also specifically included.

The antibodies and more preferably the monoclonal antibodies in question may be directed against any antigen or hapten. Preferred antibodies to be used in the present invention are directed against hormones and in particular, against gonadotrophins, such as anti-human chorionic gonadotrophin (anti-HCG), anti-follicle stimulating hormones (anti-FSH), anti-luteinizing hormones (anti-LH), anti-pregnant mares serum gonadotrophin (anti-PMSG) anti-human menopausal gonadotrophin (anti-HMG).

The usual concentrations in which the antibodies are used may vary between 0.1 and about 5 mg per ml of aqueous composition and more particularly, between 0.5 and 2.5 mg/ml. The most usual concentration is, however, between 1 and 1.5 mg per ml (of the total composition).

In general a quantity of dextran is used which may vary from 0.3 to approximately 5 parts by weight of dextran per part by weight of antibody, 1 to 2 parts by weight of dextran per 1 part by weight of antibody being regarded as the most ideal.

In an absolute sense, the quantity of dextran which is used in the present invention may vary between approximately 0.05 and 20 mg/ml of aqueous composition and more particularly, between 0.5 and 5 mg per ml of aqueous composition. A quantity of dextran of approximately 1–2 mg/ml is found to be outstandingly suitable for stabilizing an aqueous composition of 1–1.5 mg of antibody. In general, dextran is not used in such quantity that is necessary to increase the viscosity of the aqueous composition significantly.

The aqueous antibody composition suitable for injection purposes can, in addition to the constituents (antibody and dextran) already mentioned, also contain other constituents such as:

means for rendering the composition isotonic, e.g. NaCl, sorbitol, mannitol in a suitable concentration;

means for adjusting the pH of the composition to a pH between 5.0 and 9.0 and more particularly, between 7.0 and 8.5;

preservatives such as benzyl alcohol;

bactericidal substances such as the parabens;

biologically active substances such as anti-inflammatory substances, and/or anaesthetics.

The stabilized aqueous composition of, for example, monoclonal anti-gonadotrophins is prepared in the usual manner by introducing the anti-gonadotrophins concerned, dextran and any other constituents into sterilized water.

The invention is explained in more detail on the basis of the following experiment.

A solution of 1 mg per ml of monoclonal anti-HCG (mouse) in water was prepared and a certain quantity of the substance to be tested for stabilizing properties was added thereto. Each solution was kept at 4° C., 20° C. and 40° C. for one month and then assessed for the following three factors:

(1) the presence of oligomers and, in particular, of dimers,
(2) decomposition of the anti-HCG, and
(3) physical instability, in particular the appearance of opalescence and particle formation.

In the event of a positive assessment (after storage for said month) of all three factors the solution was assigned the rating (+), if all three factors were negatively assessed, the rating is specified as (−), and if one or two of the above-mentioned factors was negatively assessed, the rating ("0") has been assigned.

The results obtained after storage for one month are shown in Table I.

The substances which were assessed as still positive after one month have been studied further after 3, 6 and 9 months (see Table II).

TABLE I

| Substance tested | Quantity | Rating (1 month) |
| --- | --- | --- |
| phosphate buffer pH 8 | 0.07 molar | 0 |
| phosphate buffer pH 5.5 | 0.07 molar | 0 |
| NaCl | 9 mg/ml | |
| mannitol | 25 mg/ml | |
| glucose | 10 mg/ml | 0 |
| lactose | 10 mg/ml | −/0 |
| glycine | 1 mg/ml | |
| glycine | 23 mg/ml | 0/+ |
| arginine | 1 mg/ml | |
| dithioerythritol | 1 mg/ml | |
| PEG 400 | 50 mg/ml | 0 |
| sodium edetate | 1 mg/ml | + |
| benzyl alcohol | 10 mg/ml | 0 |
| mixture of methyl- and propylparaben | 1/0.2 mg/ml | 0 |
| benzylkonium chloride | 0.1 mg/ml | |
| dextran 40 | 1 mg/ml | + |
| ammonium chloride | 4.5 mg/ml | |
| albumin | 1 mg/ml | 0/+ |
| sodium carboxymethylcellulose | 5 mg/ml | 0 |

TABLE II

| Substance tested | Quantity | Rating, 3 months |
| --- | --- | --- |
| glycine | 23 mg/ml | |
| sodium edetate | 1 mg/ml | 0 |
| albumin | 1 mg/ml | 0 |
| dextran 40 | 1 mg/ml | + |

Even after 6 and 9 months storage the rating for dextran 40 remained positive.

EXAMPLE 1

The following composition was prepared for injection:

| | |
| --- | --- |
| monoclonal anti-HCG (mouse) | 1 mg |
| dextran 40 | 1 mg |
| NaCl | 3.5 mg |
| phosphate buffer pH = 8 | |
| Na2HPO4 | 7.5 mg |
| NaH2PO4 | 0.33 mg |
| water for injection to make | 1 ml |

This composition is stable for at least 9 months.

EXAMPLE 2

Composition for injection consisting of:

| | |
| --- | --- |
| monoclonal anti-HCG (mouse) | 1 mg |
| dextran 40 | 2 mg |
| glucose | 20 mg |
| phosphate buffer pH = 8 | |
| Na2HPO4/NaH2PO4 | 7.5 mg/0.33 mg |
| water for injection to make | 1 ml |

EXAMPLE 3

Composition for injection consisting of:

| | |
| --- | --- |
| monoclonal anti-PMSG (mouse) | 1.5 mg |
| dextran 40 | 1 mg |
| benzyl alcohol | 1 mg |
| glycine buffer pH 8.5 | |
| water to make | 1 ml |

We claim:

1. A stabilized aqueous composition of one or more monoclonal antibodies that are stabilized by dextran, comprising one or more monoclonal antibodies and 0.3 to 5 parts by weight dextran per part by weight monoclonal antibody, which dextran prevents deactivation of the monoclonal antibodies for at least one month at a temperature of 4 to 40 degrees centigrade.

2. A stabilized aqueous composition comprising monoclonal antibodies selected from the group consisting of anti-HCG, anti-FSH, anti-LH, anti-PMSG, anti-HMG, and mixtures thereof, and a sufficient amount of dextran to prevent deactivation of the monoclonal antibodies for at least one month at a temperature of 4 to 40 degrees centigrade.

3. The composition of claim 1 wherein the amount of dextran is 1 to 2 parts by weight dextran per part by weight monoclonal antibody.

4. The composition of claim 1, wherein the dextran has a mean molecular weight between 20,000 and 75,000 daltons.

5. The composition of claim 1, wherein 1 to 1.5 mg of monoclonal antibody and 1 to 2 mg of dextran are present per ml of composition.

6. The composition of claim 2, comprising the monoclonal antibody is anti-HCG.

7. The composition claim 2, comprising the monoclonal antibody is anti-PSMG.

8. The composition of claim 2, comprising dextran in an amount of 0.3 to 5 parts by weight dextran per part by weight of monoclonal antibody in said composition.

9. The composition of claim 8, wherein the amount of dextran is 1 to 2 parts by weight dextran per part by weight monoclonal antibody.

10. The composition of claim 9, wherein the dextran has a mean molecular weight between 20,000 and 75,000 daltons.

11. The composition of claim 10, wherein 1 to 1.5 milligrams of monoclonal antibody and 1 to 2 milligrams of dextran are present per milligram of composition.

12. The composition of claim 8, wherein the dextran has a mean molecular weight between 20,000 and 75,000 daltons.

13. The composition of claim 12, wherein 1 to 1.5 milligrams of monoclonal antibody and 1 to 2 milligrams of dextran are present per milliliter of composition.

14. The composition of claim 8, wherein 1 to 1.5 milligrams of monoclonal antibody and 1 to 2 milligrams of dextran are used per milliliter of composition.

15. The composition of claim 7, wherein the monoclonal antibody anti-PMSG is in an amount of 0.3 to 5 parts by weight dextran per part by weight of monoclonal antibody in said composition.

16. The composition of claim 15, wherein the amount of dextran is 1 to 2 parts by weight dextran per part by weight monoclonal antibody.

17. The composition of claim 16, wherein the dextran has a mean molecular weight between 20,000 and 75,000 daltons.

18. The composition of claim 17, wherein 1 to 1.5 milligrams of monoclonal antibody and 1 to 2 milligrams of dextran are present per milligram of composition.

19. The composition of claim 15, wherein the dextran has a mean molecular weight of between 20,000 and 75,000 daltons.

20. The composition of claim 15, wherein 1 to 1.5 milligrams of monoclonal antibody and 1 to 2 milligrams of dextran are used per milliliter of composition.

21. A method for stabilizing one or more monoclonal antibodies in an aqueous composition comprising introducing dextran to the composition in an amount of 0.3 to 5 parts by weight dextran per part by weight monoclonal antibody.

* * * * *